United States Patent
Burbank et al.

(10) Patent No.: US 8,460,228 B2
(45) Date of Patent: Jun. 11, 2013

(54) METHODS, DEVICES, AND SYSTEMS FOR PARALLEL CONTROL OF INFUSION DEVICE

(75) Inventors: Jeffrey H. Burbank, Boxford, MA (US); Joseph Turk, North Andover, MA (US); Dennis M. Treu, Bedford, NH (US); R. Michael Hofmann, Waunakee, WI (US); James M. Brugger, Newburyport, MA (US)

(73) Assignee: NxStage Medical Inc., Lawrence, MA (US)

( * ) Notice: Subject to any disclaimer, the term of this patent is extended or adjusted under 35 U.S.C. 154(b) by 75 days.

(21) Appl. No.: 12/912,714

(22) Filed: Oct. 26, 2010

(65) Prior Publication Data

US 2011/0106047 A1    May 5, 2011

Related U.S. Application Data

(60) Provisional application No. 61/255,452, filed on Oct. 27, 2009.

(51) Int. Cl.
*A61M 37/00* (2006.01)
*A61M 5/32* (2006.01)

(52) U.S. Cl.
USPC ......... 604/6.16; 604/4.01; 604/411; 604/412; 604/413

(58) Field of Classification Search
USPC ............... 604/244–246, 500, 508, 4.01, 6.09, 604/6.16, 29, 411, 412, 413
See application file for complete search history.

(56) References Cited

U.S. PATENT DOCUMENTS

| | | | |
|---|---|---|---|
| 4,810,388 | A | 3/1989 | Trasen |
| 5,420,962 | A | 5/1995 | Bakke |
| 5,705,066 | A | 1/1998 | Treu et al. |
| 7,396,359 | B1 | 7/2008 | Derowe et al. |
| 7,470,265 | B2 | 12/2008 | Brugger et al. |
| 7,540,876 | B2 | 6/2009 | Connors et al. |
| 7,662,139 | B2 | 2/2010 | Demers et al. |
| 2006/0084906 | A1* | 4/2006 | Burbank et al. ............. 604/6.16 |
| 2008/0208103 | A1 | 8/2008 | Demers et al. |
| 2009/0012448 | A1 | 1/2009 | Childers et al. |
| 2009/0182263 | A1* | 7/2009 | Burbank et al. ................ 604/28 |
| 2009/0270832 | A1 | 10/2009 | Vancaillie et al. |
| 2010/0063456 | A1 | 3/2010 | Rahimy et al. |

FOREIGN PATENT DOCUMENTS

| | | |
|---|---|---|
| WO | WO 03105944 A1 | 12/2003 |
| WO | WO 2008058656 A1 | 5/2008 |
| WO | WO 2008125893 A1 | 10/2008 |
| WO | WO 2009006507 A1 | 1/2009 |
| WO | WO 2009094183 A1 | 7/2009 |
| WO | WO 2009094186 A1 | 7/2009 |
| WO | WO 2009131742 A1 | 10/2009 |

* cited by examiner

*Primary Examiner* — Kevin C Sirmons
*Assistant Examiner* — Imani Hayman
(74) *Attorney, Agent, or Firm* — Mark A. Catan; Miles & Stockbridge P.C.

(57) ABSTRACT

A tubing set is disclosed including a first line having first and second ends, a bag spike at the first end configured for connection to a source of infusate, and a connector at the second end configured for connection to a blood line. The first line has a pumping portion for engagement with an infusate pump. The tubing set includes a second line having first and second ends, the first end being attached to the first line between the first line pumping portion and the first line second end and the second end being configured for connection to the first line between the first line first end and the first line pumping portion. The second line second end is configured for connection to the first line by a dual lumen spike.

7 Claims, 6 Drawing Sheets

Prior art

Fig. 1

Prior art

Prior art

METHODS, DEVICES, AND SYSTEMS FOR PARALLEL CONTROL OF INFUSION DEVICE

This application claims the benefit of U.S. Provisional Application No. 61/255,452, entitled "Methods, Devices, and Systems for Parallel Control of Infusion Device," filed on Oct. 27, 2009, which is incorporated herein by reference in its entirety.

Embodiments generally relate to infusion device control and, more particularly, to the control and/or sensing of the fluid conveyance (e.g. infusion) of one device (such as an infusion pump) by another device so as to provide control and/or sensing of fluids, for example, in an extracorporeal blood treatment system.

Infusion of medicaments and/or drugs may be provided in parallel with the administration of a blood treatment, such as dialysis. In such circumstances, it may be necessary for a medical practitioner or patient to continuously monitor and operate two pieces of equipment. The present invention was conceived in view of the above needs, among other things.

According to one or more embodiments of the disclosed subject matter, a tubing set has a first line having a bag spike at a first end thereof configured for connection to a source of infusate. The first line has a connector at a second end thereof configured for connection to a blood line. The first line has a pumping portion for engagement with an infusate pump. A second line has first and second ends. The second line first end is attached to the first line between the first line pumping portion and the first line second end and the second line second end is configured for connection to the first line between the first line first end and the first line pumping portion. A check valve is located in the second line, the check valve having a predetermined cracking pressure (e.g., of at least 200 mm Hg). The second line second end is configured for connection to the first line by a dual lumen spike such that when a container is connected to the dual lumen spike, a bypass loop is formed that permits a flow from a second end side of the pumping portion to the first end side of the pumping portion. The first line includes a spike and spike septum at the first end thereof.

According to one or more embodiments of the disclosed subject matter tubing set has a dual lumen bag spike has a sharp end and a connector end, the dual lumen bag spike has first and second lumens each opening on a side toward the sharp end and first and second connectors at the connector end. A junction connector has first, second, and third ports. The dual lumen bag spike first connector has a first check valve with a cracking pressure (e.g., at least 100 mm Hg) and a bypass line inline with the first check valve, a terminal end of the bypass line being connected to the junction connector first port. The terminal end is remote from the dual lumen bag spike. The junction connector second port has an infusate line connector configured for connection to an infusate line. The junction connector third port is configured for connection to a secondary infusate line. The dual lumen bag spike second connector has a spike septum for connection to a single lumen bag spike of an infusate line. A secondary infusate line may be connected to the junction connector third port at a first end thereof; the secondary infusate line has a second end configured for connection to a blood line. The secondary infusate line may have a clamping portion configured for engagement with a control valve of an extracorporeal blood treatment machine. The secondary infusate line may have a check valve with a predetermined cracking pressure (e.g., at least 100 mm Hg).

According to one or more embodiments of the disclosed subject matter, a method of flowing infusate includes flowing infusate with an infusion pump into a tubing set for an extracorporeal blood processing machine. The method further includes clamping an infusate line to halt the flow of infusate into the tubing set for the extracorporeal blood processing system while permitting the infusion pump to continue pumping infusate. A check valve opens with a pressure of at least 100 mm Hg which is generated by the infusion pump. The opening of the check valve opens a bypass line and thereby causes circulation of infusate through the bypass line. The clamping further includes halting the flow of blood in the tubing set for an extracorporeal blood processing system. The clamping and halting may include simultaneously closing infusate and blood tubes with a single clamping member. The clamping and halting may be performed by an extracorporeal blood treatment machine which is separate from the infusion pump. The method may further include restarting a flow of blood with the extracorporeal blood treatment machine by unclamping a blood line, the unclamping being effective to unclamp the infusate line thereby closing the check valve.

DETAILED DESCRIPTION

Figure 1:
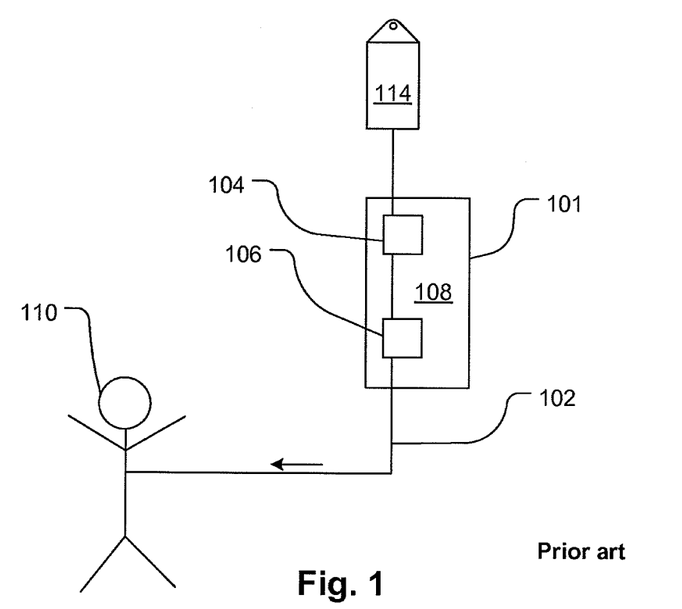
FIG. 1 shows an infusion pump and tubing set according to the prior art.

FIG. 1 shows an infusion system 101 having an infusion pump 108 and a tubing set 102 according to the prior art. The infusion pump 108 may have one or more active and/or passive actuators 104, including at least a pump, such as a peristaltic pump (not shown) and a tubing clamp (not shown) that acts as a cutoff valve. The pump 108 may be connected to an infusate container 114 and may also have one or more sensing devices 106 such as an air sensor. The pump 108 may include a controller (not shown) that allows pumping rate, start and stop times, and other control parameters to be adjusted and programmed. The tubing set may be connected to a patient 110 by means of any suitable vascular access device.

Figure 2:
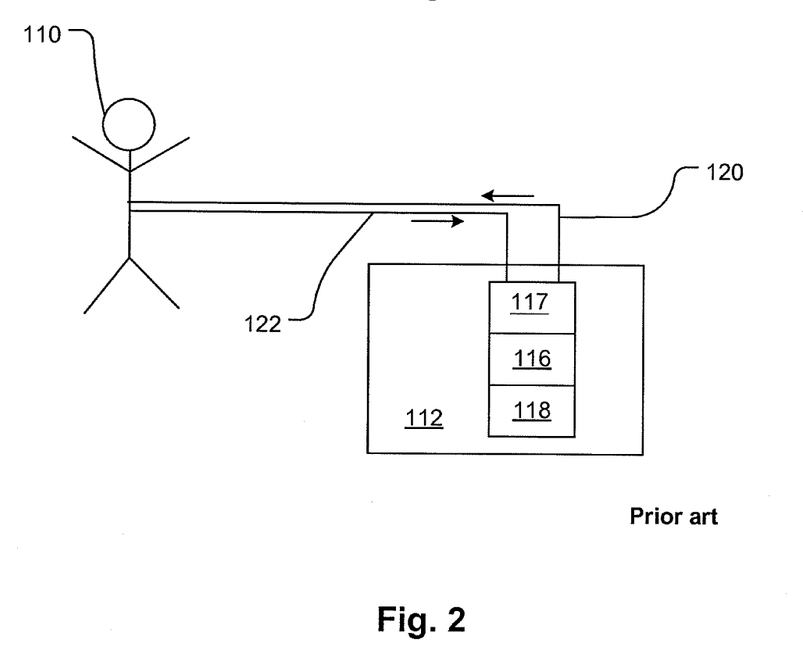
FIG. 2 shows a medical treatment system and tubing set according to the prior art.

FIG. 2 shows an extracorporeal blood treatment machine 112 that delivers a therapeutic treatment to a patient 110. Blood is drawn from the patient 110 by a pump (not shown) through a blood tubing set 120, 122 and conveyed through flow control 117 (including, for example, one or more tubing clamps to halt flow), sensing 116, and treatment 118 elements of the machine 112. The tubing set 120, 122 may have venous 120 and arterial 122 portions, where blood is returned to the patient and removed, respectively. A controller (not shown) of the blood treatment machine may perform various functions including instantaneous operator commands. The machine 112 may also clamp the blood tubing and/or halt the blood pump in response to detected conditions, preprogrammed treatment intervals, or any other purpose.

Figure 3:
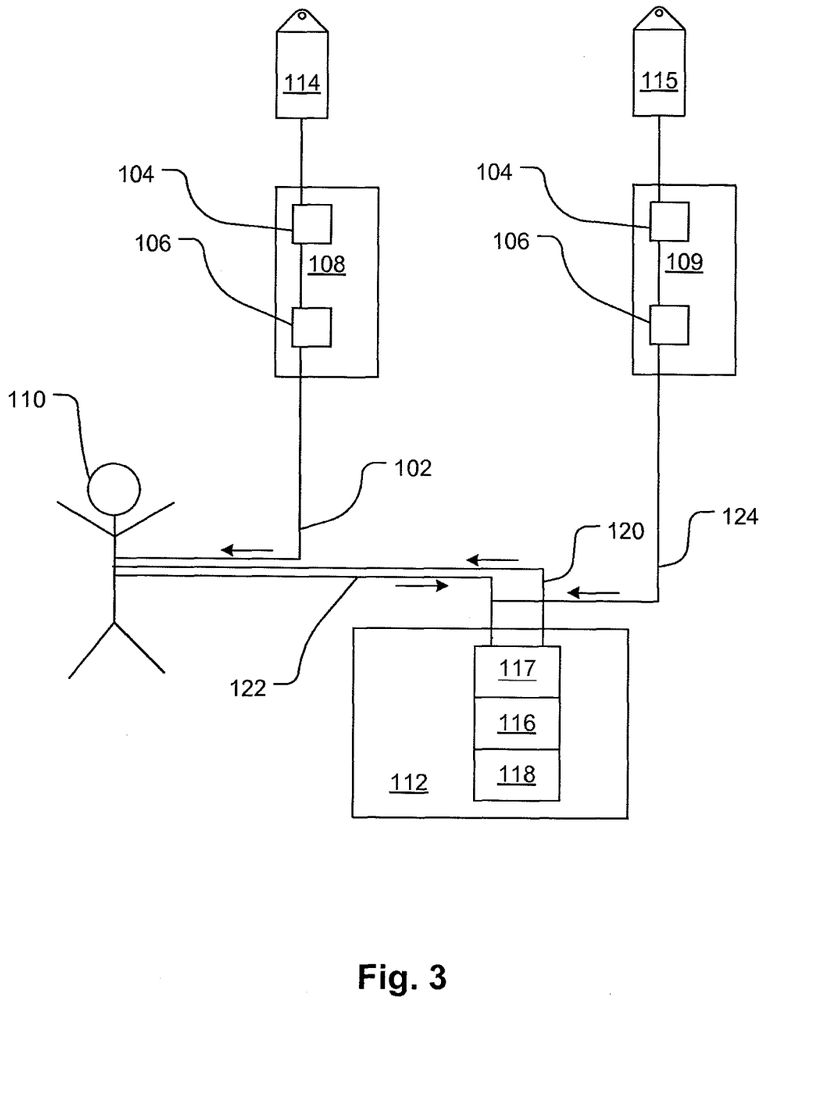
FIG. 3 shows the use of infusion pumps for direct infusion into a patient and the infusion of medication or medicaments into a venous blood line of a blood treatment system, which infusion pumps may be used separately or simultaneously.

FIG. 3 shows an extracorporeal blood machine 112 with infusion pumps 108 and 109. The infusion pumps 108 and 109 may be configured similar to the infusion pump 108 of FIG. 1 and may be connected to infusate containers 114 and 115, respectively. The extracorporeal blood machine 112 may be configured similar to the extracorporeal blood machine of FIG. 2. The infusion pump 108 pumps fluid such as medicament and/or drugs into a patient 110. Alternatively the infusion pump 108 may pump the fluid into the venous line 120 of the extracorporeal blood circuit 120, 122. The infusion pump 109 has an infusion tubing set 124 that is attached to the arterial line 122 of the blood circuit and is configured to pump fluid into the arterial line 122. For example, the infusion pump 109 may flow an anticoagulant and/or predilution medicament or other fluid.

Figure 4:
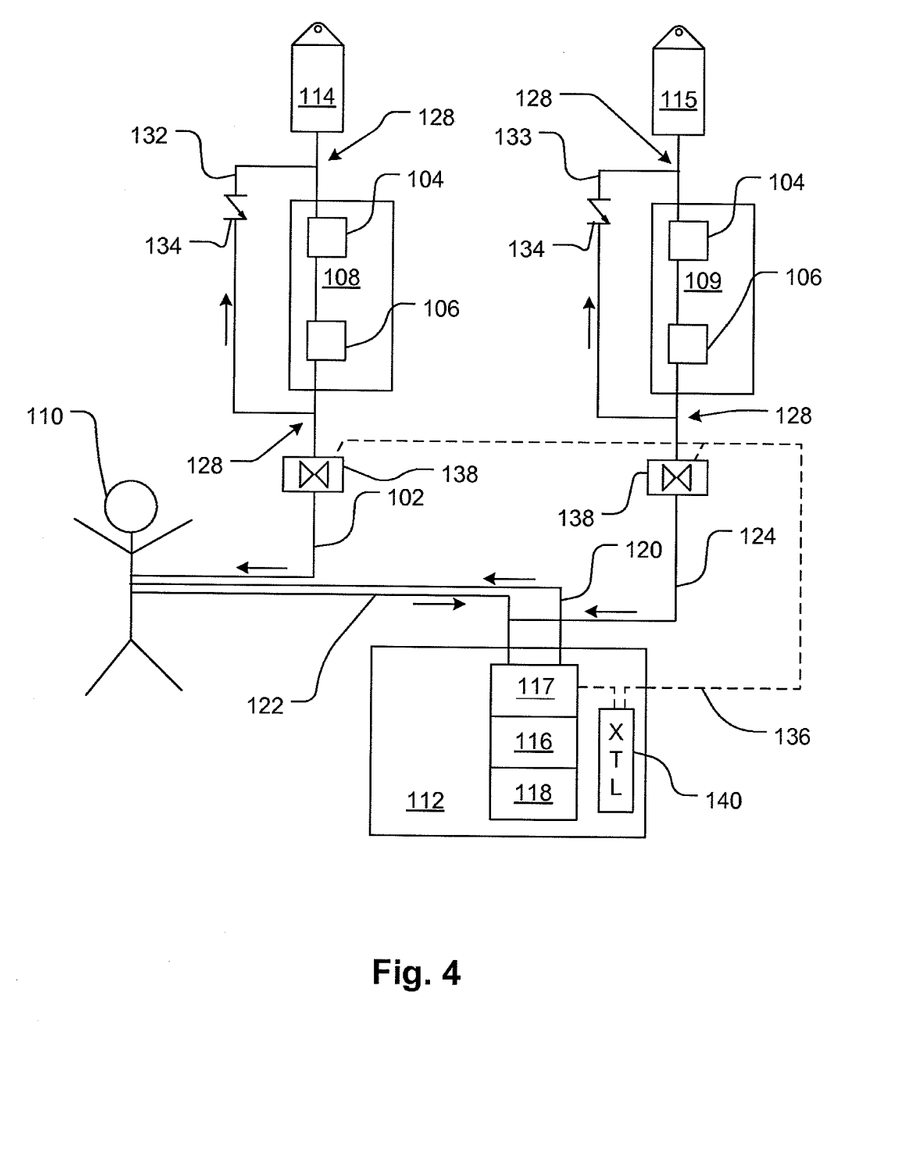
FIG. 4 shows a system in which infusion pumps are controlled by a blood treatment machine through an active intermediate flow control mechanism according to embodiments of the disclosed subject matter.

Referring to FIG. 4, the extracorporeal blood treatment machine 112 with infusion pumps 108 and 109 similar to the configuration of FIG. 3 with additional features permitting the extracorporeal blood treatment machine 112 to control the infusion pumps (108 and 109). In the embodiment of FIG. 4, a bypass circuit 132 with an inline check valve 134 connects the outlet portion of the infusion tubing set 102 to an inlet portion thereof. A bypass circuit 133 with an inline check valve 134 connects the outlet portion of the infusion tubing set 124 to an inlet portion thereof. Control valves 138 are arranged to regulate the flow of fluid in each of the infusion tubing sets 102 and 124 responsively to a control signal from a controller 140 of the extracorporeal blood treatment machine 112. The controller 140 may be the controller referenced above that regulates the functions of the extracorporeal blood treatment machine 112 including pump speed, clamping of tubing, receiving and processing sensor signals, etc. The control signal may be conveyed to the control valves 138 by a data signal line 136, a final control drive current, or any other suitable mechanism that permits the controller 140 to regulate, including stopping and starting, the flow in the infusion tubing sets 102 and 124.

The check valves 134 may have a predetermined cracking pressure that is high enough to allow the infusion pumps 108 and 109 to infuse fluid without causing recirculation of fluid in the bypass circuit 132 or 133. However, the cracking pressure is low enough that when the extracorporeal blood treatment machine 112 halts the flow of fluid in either or both of the infusion tubing sets 102 and 124, the cracking pressure is overcome and fluid circulates in the bypass circuit 132, 133. The cracking pressure may also be low enough to permit the infusion pumps to continue operating without triggering any overpressure lockout or alarm.

Figure 5:
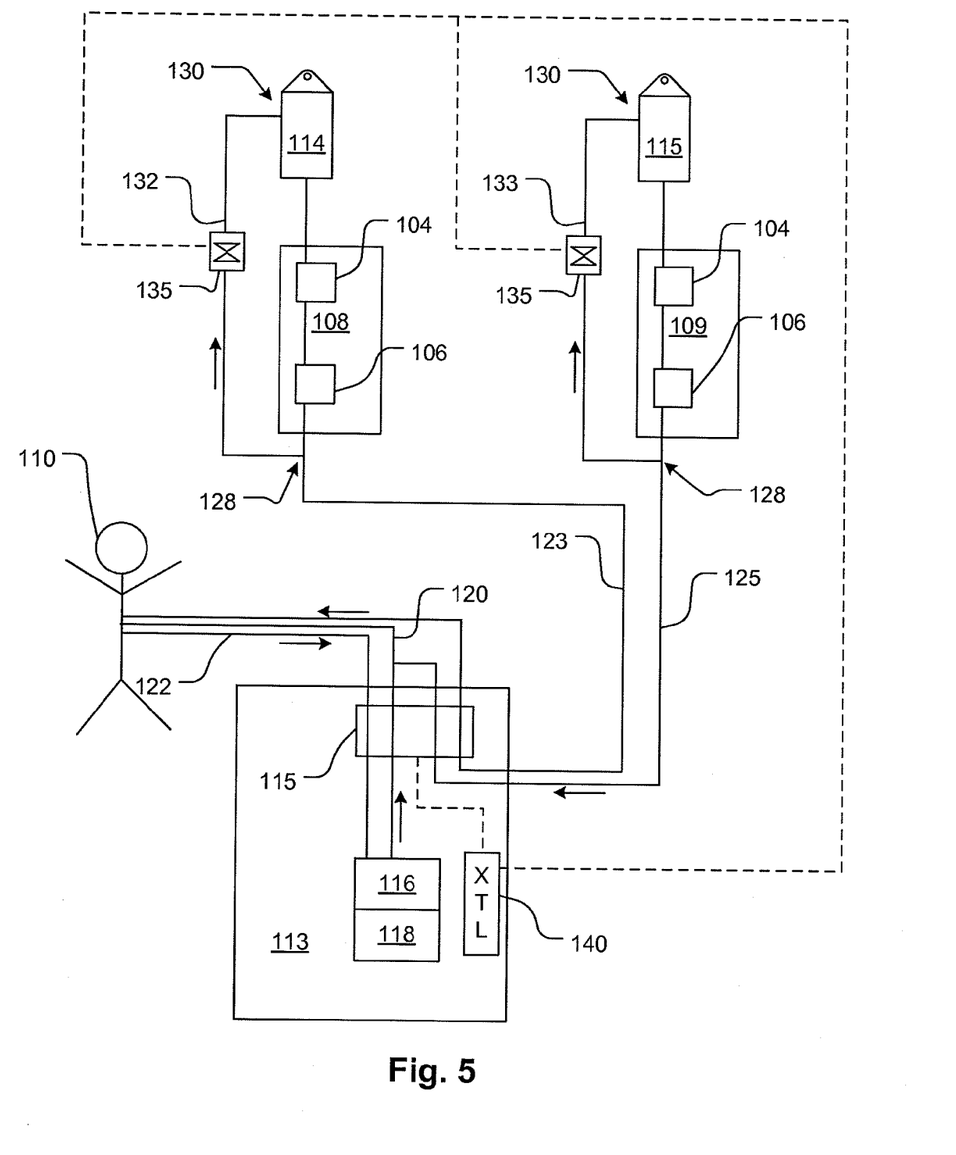
FIG. 5 shows a system in which infusion pumps are controlled by one or more actuators of a blood treatment machine according to embodiments of the disclosed subject matter.

Referring to FIG. 5, an extracorporeal blood treatment machine 113 with infusion pumps 108 and 109 similar to the configuration of FIG. 4 with the substitution of features that permit the extracorporeal blood treatment machine 112 to control the infusion pumps. In the present embodiment, the flow through the bypass circuits is selectively blocked or permitted by control valves 135 which are controlled by the extracorporeal blood treatment machine controller 140. When the extracorporeal blood treatment machine 113 stops blood flow by means of its flow regulator 115, for example, it may transmit a signal to the control valve 135 to open one or both of the respective bypass lines.

Alternatively, a sensor (not shown) may be provided to detect the halting of flow in the blood lines, for example, a flow sensor, a pressure sensor, a current sensor that detects blood pump motor current or other means. To halt and permit the flow of infusate in infusion tubing sets 123 and 125, the infusion lines may be run through a same flow regulator 115 as used to control the flow of blood in the extracorporeal blood treatment machine 113. The latter may be provided without necessarily providing a modified extracorporeal blood treatment machine by placing the lines close together under an existing tubing clamp, for example.

The mechanisms for halting and permitting the flow of fluid in the bypass lines (control valves 135 versus check valves 134) may be substituted between the embodiments of FIGS. 4 and 5 and other embodiments described herein. Also, the mechanism for controlling the flow of fluid in the infusion tubing set lines 123 and 125 are alternatives that can be substituted in either embodiment of FIGS. 4 and 5 or modified embodiments described herein. Also, as shown in FIGS. 4 and 5, either T junctions 128 or ports 130 opening into the infusate containers 114, 115 may be used to provide for the flow in the bypass line in any of the described embodiments. Note that although the term infusate container is used to identify containers 114 and 115 (and other similar elements) and the term infusate is used to identify the fluid pumped by the infusion pumps, it is also possible that these contain medicaments that are not necessarily infused into the patient. For example, they may contain a prediluent, most or all of which is filtered out by hemofiltration.

Figure 6:
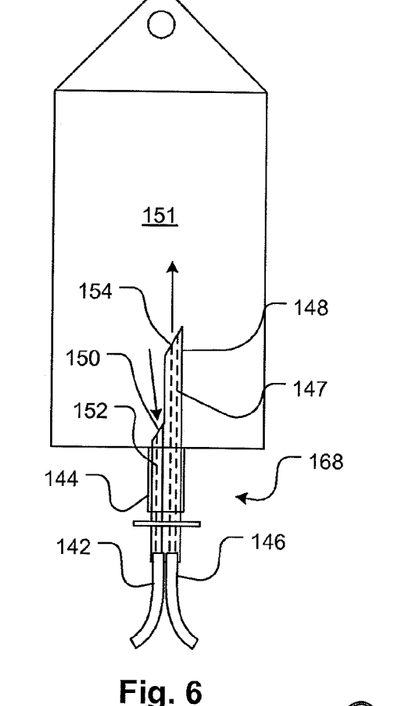
FIG. 6 shows a dual lumen catheter inserted in a source of infusate according to embodiments of the disclosed subject matter.

Referring to FIG. 6, a dual lumen spike 168 may be used to provide branching lines 142 and 146 each having access to an infusate container 151. Thus the dual lumen spike may perform the function of a T junction 128 or ports 130 described above allowing for the creation of a bypass loop. The dual lumen spike 168 has a spike 148 with first 152 and second 147 lumens. The spike fits in a septum 144 to seal the openings 150 and 154 which are located at different levels when inserted vertically. The flow is preferably arranged such that fluid enters the container at a higher level than fluid leaving thereby permitting any bubbles to settle out.

Figure 7:
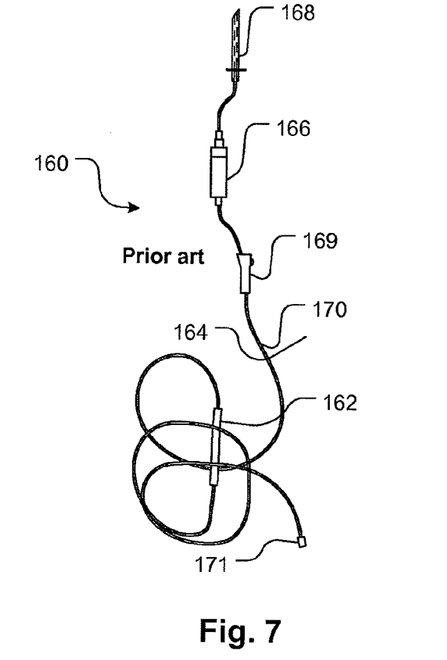
FIG. 7 shows a tubing set for infusion according to the prior art.
Figure 8:
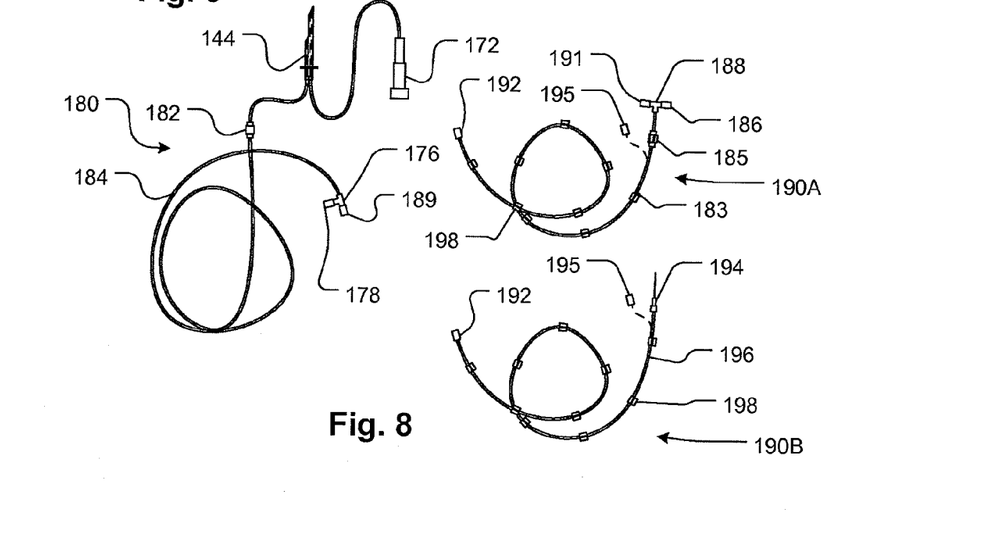
FIG. 8 shows a tubing set for controlling the infusion by one or more independent infusion pumps using another device according to embodiments of the disclosed subject matter.

Referring to FIG. 7, a conventional infusion tubing set 160 may having a bag spike 168, a drip chamber 166, a flow regulator 169, a flexible line 170, a pumping portion 162, and a terminal connector 171, such as a luer connector. Referring to FIG. 8, an auxiliary tubing set 180 is adapted to form a bypass line with the conventional infusion tubing set of FIG. 7. A bag spike septum 172 permits the tubing set 180 to be connected to the bag spike 168 of the infusion tubing set 160. Alternatively, an infusion tubing set 160 that has another type of connector such as a luer may also be provided in which case the septum 172 may be substituted with a suitable mating connector. A check valve 182 provides the function of check valve 134 described above. A tubing line 184 provides a bypass loop. A T junction 176 has connectors, one of which 178 may be connected to the connector 171 of tubing set 160, thereby completing the bypass line configuration described above. To connect an infusion output connector 189 to either the patient for infusion or either the arterial or venous line of the extracorporeal treatment machine, an additional line, for example, 190A or 190B may be integrally attached to port T junction 176 or connected by a connector 192 to the connector 189. A tube 196 is of sufficient length to reach an infusion point. For direct infusion, a cannula 194 may be preconnected or integral to the tube 196. Alternatively, a connector 195 may be provided for connection to a patient access or the venous line of the blood treatment machine tubing set. For connection to a venous line of a blood treatment machine tubing set, a T junction 188 may be provided with connectors 191 and 186 for connection between the patient access and the arterial branch of a blood line. A check valve may be provided with a cracking pressure that prevents outflow from the venous line which may be under positive pressure. Supports 198 may be provided at intervals along the line to allow the lines 196 to attach to other adjacent lines, such as illustrated in FIG. 9, described below.

Figure 9:
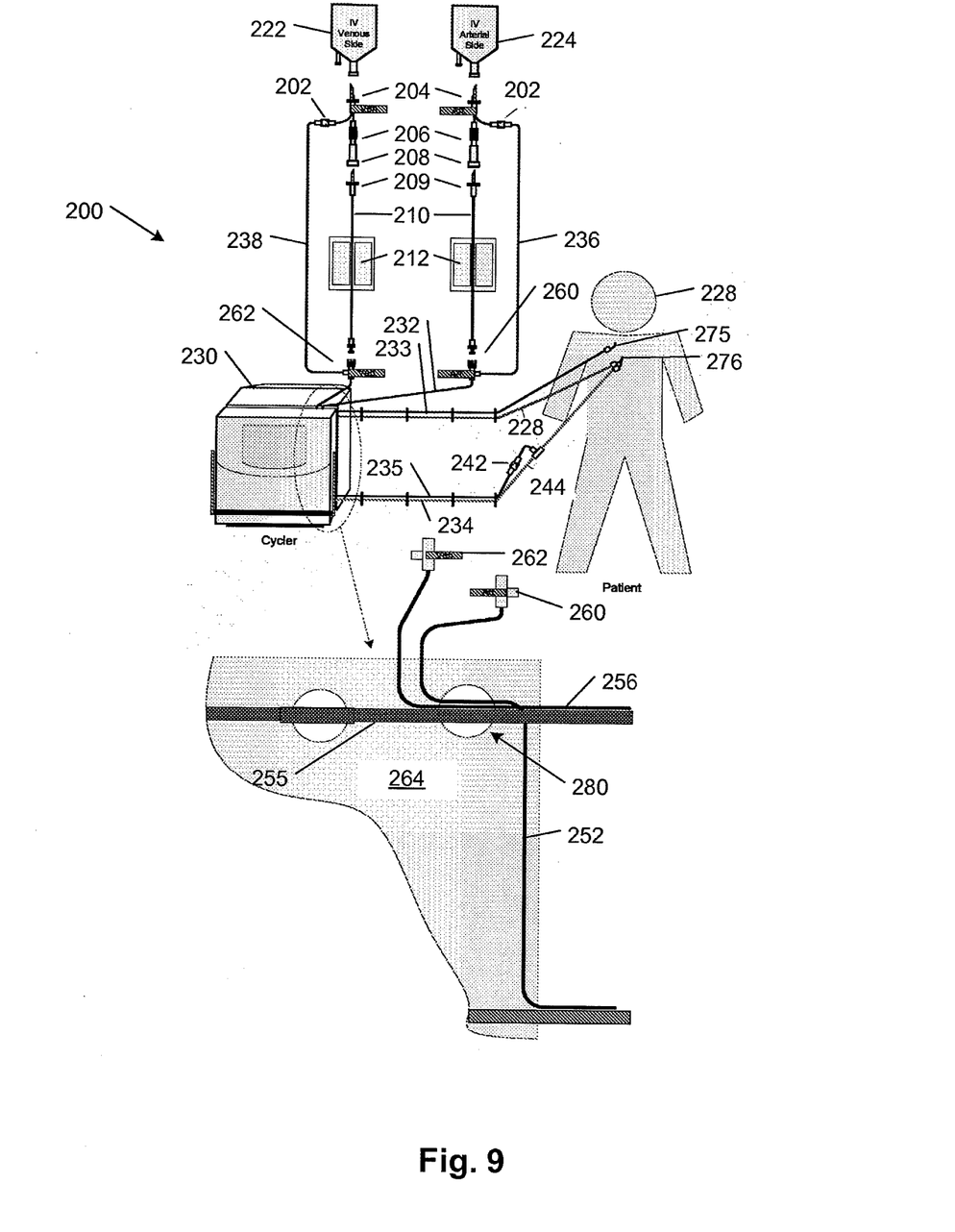
FIG. 9 shows a system in which infusion pumps are controlled by one or more actuators of a blood treatment machine according to embodiments of the disclosed subject matter.

Referring to FIG. 9, an extracorporeal blood treatment machine 230 with infusion pumps 212 is similar to the configuration of FIG. 5. Infusate (and/or medicament) containers 222 and 224 are accessed by dual lumen spikes 204 which branch to bypass loops 238 and 236, respectively. A connector pair 206 connects a septum 208 to allow connection to conventional bag spikes 209 thereby connecting to infusion tubing sets 210. The latter run through respective ones of the infusion pumps 212 and join with bypass loops 238, 236 by T junctions 262 and 260. Infusion lines 230 and 232 connect to blood lines or a patient 228 and run under a flow control valve 280 such as a tubing clamp of the blood treatment machine 230. The control valve 280 may be the same clamp as used to block flow in one of the blood lines 255 of the blood treatment machine 230.

The blood treatment machine 230 has venous and arterial lines 228 and 234 respectively. A positive pressure in line 234 is compensated by providing a check valve 242 whose cracking pressure must be overcome to allow flow into the blood line 234. A cartridge tray 264 supports the blood treatment machine tubing set for placement in the blood treatment machine 230. Infusion line branch 233 is used for direct infusion. Infusion line 235 flow infusate into a blood line 244. Vascular accesses 274 and 276 are provided according to known principles and techniques.

In the foregoing embodiments, the infusion pump may be permitted to continue operating even though the extracorporeal blood machine occludes the infusion line by a control valve such as an automatic tubing clamp as discussed. This is permitted because the infusion pump may pump fluid in the bypass line by overcoming the cracking pressure (or when the control valve is opened by a signal) and the fluid is circulated. The cracking pressure of a check valve may be selected to ensure the overpressure threshold of the infusion pump is not exceeded to permit bypass flow. In any of the foregoing embodiments, the bypass loop may be omitted and the infusion line occluded as described. In such embodiments, the infusion pump's own overpressure controls may be relied upon to halt the pumping process. In such embodiments, the infusion pump may need to be restarted by an operator or the infusion pump may be programmed to restart automatically upon release of the occlusion caused by the blood treatment machine.

While exemplary forms of the invention have been disclosed, it will be apparent to those skilled in the art that various changes and modifications may be made that will achieve some of the advantages of the invention without departing from the spirit and scope of the invention. It will be apparent to those reasonably skilled in the art that other components performing the same function may be suitably substituted. Although specific embodiments of the invention have been described, various modifications, alterations, alternative constructions, and equivalents are also encompassed within the scope of the invention. The described invention is not restricted to operation within specific treatment environments and may be used to interface other kinds of fluid systems for medical treatments. Further, while the present invention has been described using a particular combination of components and systems, it should be recognized that other combinations of hardware and software are also within the scope of the present invention. Therefore, the scope of the invention is to be determined solely by the appended claims.

What is claimed is:

1. A tubing set comprising:
a dual lumen bag spike having a sharp end and a connector end, the dual lumen bag spike having first and second lumens each opening on a side toward the sharp end and first and second connectors at the connector end; and
a junction connector having first, second, and third ports, the dual lumen bag spike first connector having a first check valve with a cracking pressure of at least 100 mm Hg and a bypass line inline with the first check valve, a terminal end of the bypass line being connected to the junction connector first port, the terminal end being remote from the dual lumen bag spike,
the junction connector second port having an infusate line connector configured for connection to an infusate line,
the junction connector third port being configured for connection to a secondary infusate line, and
the dual lumen bag spike second connector having a spike septum for connection to a single lumen bag spike of an infusate line.

2. The tubing set of claim 1, further comprising a secondary infusate line connected to the junction connector third port at a first end thereof, the secondary infusate line having a second end configured for connection to a blood line; the secondary infusate line having a clamping portion configured for engagement with a control valve of an extracorporeal blood treatment machine.

3. The tubing set of claim 2, wherein the secondary infusate line has a check valve having a cracking pressure of at least 100 mm Hg.

4. A method of flowing infusate comprising:
flowing infusate with an infusion pump into a tubing set for an extracorporeal blood processing machine having a controller configured to control an external device for clamping a fluid line; and
clamping an infusate line by the external device, to halt the flow of infusate into the tubing set for the extracorporeal blood processing machine, under control of the controller of the extracorporeal blood processing machine;
wherein the clamping includes clamping the infusate line and a blood line of the extracorporeal blood processing machine by the external device; and
wherein the infusion pump is separate from the extracorporeal blood processing machine such that the flow therefrom is controlled exclusively by the clamping of its own external device for clamping through the controller of the extracorporeal blood processing machine without controlling the infusion pump otherwise.

5. The method of claim 4, wherein the clamping and halting include simultaneously closing infusate and blood tubes with a single clamping member.

6. The method of claim 4, wherein the clamping and halting are performed by the extracorporeal blood treatment machine.

7. The method of claim 4, further comprising restarting a flow of blood with the extracorporeal blood treatment machine by unclamping the blood line, the unclamping being effective to unclamp the infusate line, and closing a check valve with a pressure of at least 100 mm Hg generated by the infusion pump to open a bypass line to circulate infusate through the bypass line.

* * * * *